United States Patent [19]

Bothwell

[11] Patent Number: 4,969,473

[45] Date of Patent: Nov. 13, 1990

[54] DENTAL PATIENT FACE AND NECK SHIELD

[76] Inventor: Susan F. Bothwell, 1041 Blue Ridge Ave., NE. Terrace Apt., Atlanta, Ga. 30306

[21] Appl. No.: 169,448

[22] Filed: Mar. 17, 1988

Related U.S. Application Data

[63] Continuation-in-part of Ser. No. 14,282, Feb. 13, 1987, abandoned, and a continuation-in-part of Ser. No. 756,949, Jul. 19, 1985, abandoned.

[51] Int. Cl.$^5$ ............................................. A61F 9/00
[52] U.S. Cl. .................................... 128/858; 128/863; 433/136
[58] Field of Search ..................... 128/205.24, 201.25, 128/201.26, 201.22, 206.12, 206.14, 206.18, 260.19, 139, 132 D, 132 R, 206.22, 207.23, 208.25; 433/130, 132; 132/88.5; 2/9, 173, 205, 206

[56] References Cited

U.S. PATENT DOCUMENTS

| | | | |
|---|---|---|---|
| 1,635,275 | 7/1927 | Johnson | 128/132 R |
| 1,795,866 | 3/1931 | King | 128/139 |
| 1,800,051 | 4/1931 | Blanco | 128/201.25 |
| 2,527,726 | 10/1950 | Hendrix | 132/88.5 |
| 2,695,622 | 11/1954 | Herod et al. | 132/88.5 |
| 3,478,432 | 11/1969 | Gross | 433/137 |
| 3,781,994 | 1/1974 | Hesselgren | 433/137 |
| 3,799,161 | 3/1974 | Collins | 128/132 D |
| 3,828,366 | 8/1974 | Conrad | 2/9 |
| 4,038,979 | 8/1977 | McCosker | 128/206.12 |
| 4,259,748 | 4/1981 | Miller | 2/9 |
| 4,296,746 | 10/1981 | Mason, Jr. et al. | 128/206.12 |
| 4,344,758 | 8/1982 | Wielhouwer et al. | 433/136 |
| 4,626,211 | 12/1986 | Coston | 433/133 |

FOREIGN PATENT DOCUMENTS

| | | | |
|---|---|---|---|
| 119914 | 4/1961 | Fed. Rep. of Germany | 128/132 R |
| 374693 | 1/1907 | France | 128/139 |
| 493333 | 8/1919 | France | 128/206.12 |
| 1072905 | 9/1954 | France | 128/132 R |
| 3083 | of 1867 | United Kingdom | 128/139 |
| 13394 | of 1911 | United Kingdom | 433/136 |

*Primary Examiner*—Randall L. Green
*Assistant Examiner*—K. Reichle
*Attorney, Agent, or Firm*—Vivian L. Steadman; Harry I. Leon

[57] ABSTRACT

A disposable shield stretching from the top of a wearer's head to his neck and including a mouthpiece which can be sealed to the skin, with the seal being disposed proximate to and extending along the entire length of the outer edges of an individual's lips. The mouthpiece is adapted to allow both of the lips to protrude through an opening in the shield when a person is holding his mouth wide-open as is required of dental patients. The shield further includes at least one panel of an air permeable, absorbent material situated contiguous with a wearer's nostrils to allow ample ventilation while simultaneously preventing the passage and subsequent inhalation or deposition on the eyes, skin, or hair of sodium bicarbonate- and debris-laden mists which are routinely deflected from a patient's mouth during the course of dental procedures.

4 Claims, 4 Drawing Sheets

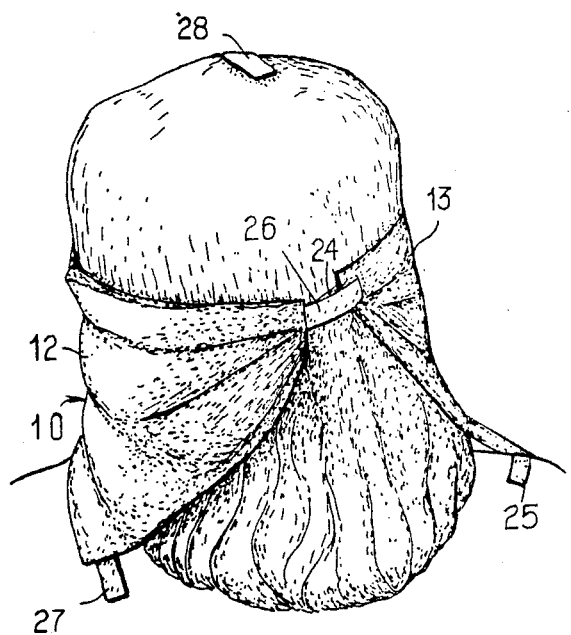
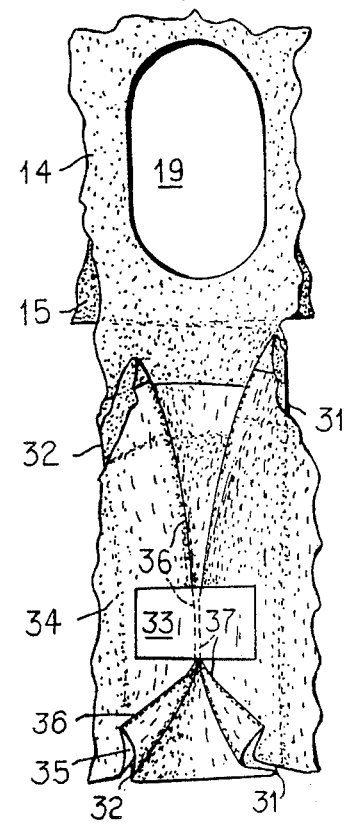
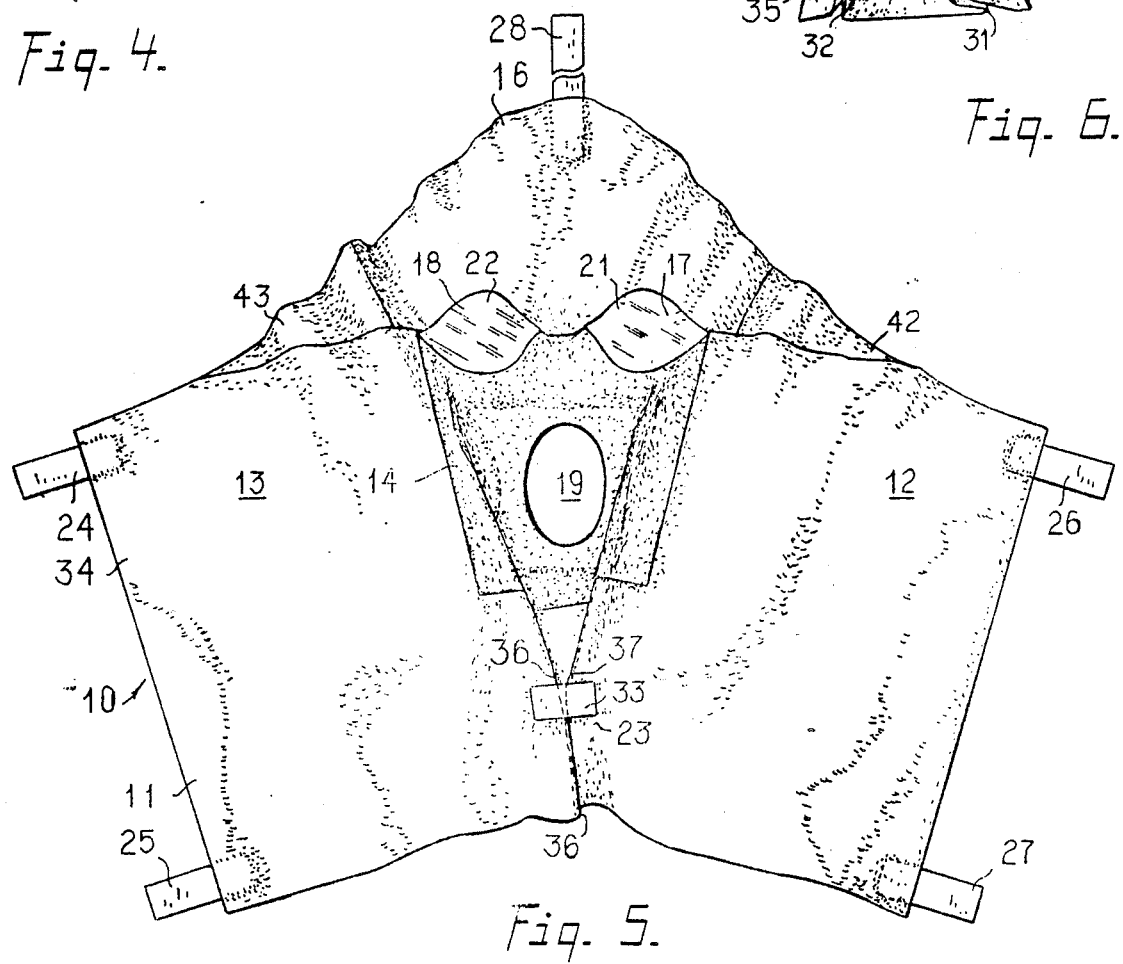

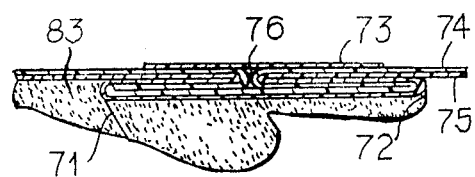
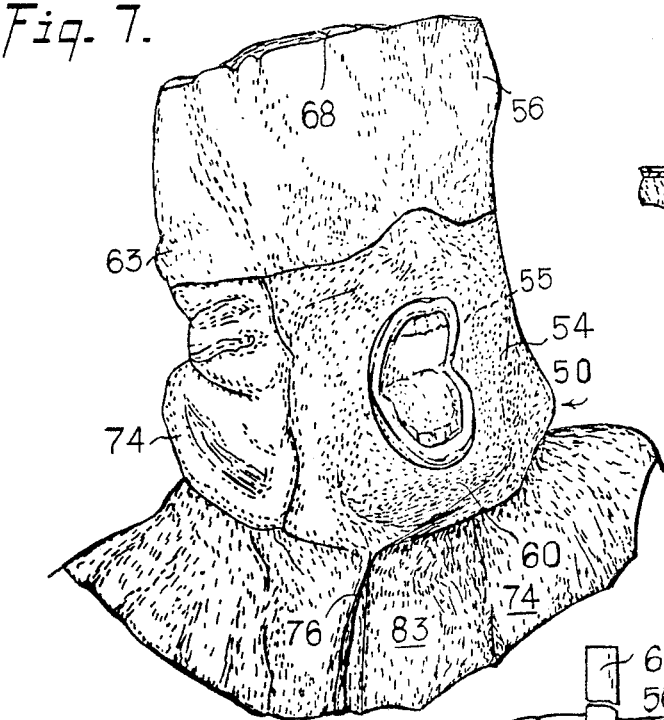
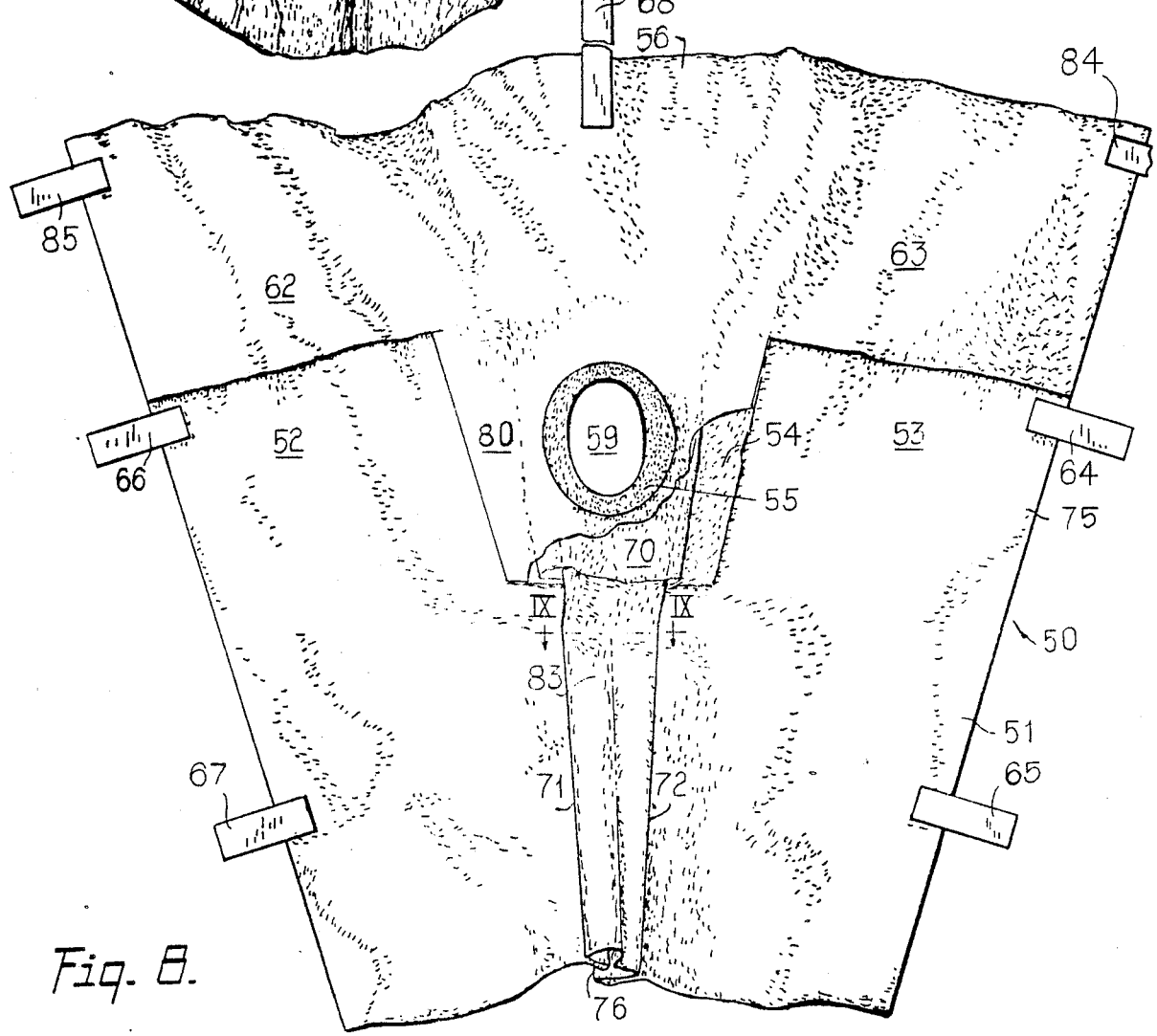

DENTAL PATIENT FACE AND NECK SHIELD

CROSS REFERENCE TO RELATED APPLICATION

This application is a continuation-in-part of my earlier copending application, Ser. No. 014,282, filed Feb. 13, 1987, and of my application, Ser. No. 756,949, filed Jul. 19, 1985, both now abandoned.

BACKGROUND OF THE INVENTION

1. Field of the Invention

This invention relates to face masks and more particularly to a disposable device for the protection of the eyes, face, hair, neck and upper respiratory system of a patient undergoing a dental procedure.

2. Description of the Prior Art

A popular method employed by dental hygienists to clean and polish teeth involves spraying a solution of sodium bicarbonate at a high pressure. Once the dislodgement of plaque has been initiated with the use of a high speed drill or of manual scraping tools, the bicarbonate solution is applied in the form of a small, continuous jet of liquid to finish the process. Unfortunately, the action of the jet also causes bacterial agents and other debris to escape from the patient's mouth as a mist which contaminates the surrounding atmosphere.

Common practice has been for the technician to cover only the upper portion of an individual's torso prior to a dental hygiene procedure, with his face, hair, and most of his neck remaining exposed. Unprotected by any facial mask, the patient is obliged to inhale air laden with bacteria and debris from his own mouth. Moreover, the individual's face and hair become coated with a film of sodium bicarbonate which may cause eye and skin irritation as well as a disarray of his or her hairdo and of any makeup being worn.

Disposable devices which cover the entire face of a person are known in the prior art, but each of them lacks an opening allowing access to the mouth which can be isolated so as to cause matter exiting the wearer's mouth and carried by the air to take a circuitous path through a filter before reaching the remainder of his face.

SUMMARY OF THE INVENTION

A main object of the invention is to provide a device to protect the eyes, hair and upper respiratory system of a dental patient from the mist of fine droplets leaving his mouth which would otherwise impinge upon his person when a jet spray of an abrasive solution is directed at his teeth to clean and polish them.

A further object of this invention is to provide means for holding a person's mouth wide-open during a dental hygiene procedure as an aid to both the patient and the operator.

A still further object of this invention is to provide such a device which is sufficiently inexpensive as to be considered disposable after each use.

In accordance with the invention, a mouthpiece having a first opening which is elongated and generally oval in shape is affixed to the peripheral edges of a second opening formed in a body of flexible material shaped to cover the face of a wearer except for the mouth. The mouthpiece has a pressure-sensitive adhesive coating which surrounds the first opening and which is disposed at least substantially at the edge thereof so that the mouthpiece can be made to adhere to the skin bounding the lips of a wearer and to form a seal between the mouthpiece and the skin surrounding the lips. Disposed proximate the mouthpiece is a central panel of air permeable material which is impermeable to the bulk of mists impinging on the device during standard dental procedures. The central panel is joined to a main body panel which has side wings and a section which extend laterally and downwardly, respectively, from the central panel. The material of which the main body panel is formed and the junctures between it and the central panel are at least as impervious to mists as is the central panel. The central panel comprises means for filtering air exiting the mouth of the wearer before it reaches his nose.

To insure that the air breathed through the wearer's nostrils must first pass through the filtering means, there is provided a section of flexible material which extends downwardly from the panel of air permeable, mist impermeable material and which is folded upon itself twice to form a pair of pleats on either side of a centerline which bisects the device approximately symmetrically. Parts of the outer edges of the two pairs of pleats so formed are contiguous with each other and are permanently fixed together along the centerline so that the pleats form a chamber which is adapted to receive a wearer's chin. Such a chamber permits the freedom of motion which a person's head must have during dental procedures to allow him to expectorate excess saliva and debris properly. As a wearer's head is turned from side to side, his chin remains in the chamber; and the pleats forming it afford sufficient slackness so that the entire body of the device does not have to turn with the head, thereby aiding in maintaining intact the seal between the mouthpiece and the wearer's skin throughout the procedure.

BRIEF DESCRIPTION OF THE DRAWINGS

Further details are explained below with the help of the examples illustrated in the attached drawings in which:

FIG. 4 is a perspective view of the back side of the head of a person wearing the shield according to FIG. 1;

FIG. 5 is a plan view of the shield according to FIG. 1 viewed from the front;

FIG. 6 is an enlarged frontal view of a fragmentary portion of a section of the shield which is disposed downwardly of the mouthpiece along the line III—III of FIG. 2, parts of two pairs of folds being spread apart for clarity of illustration;

FIG. 7 shows the same face and neck shield as in FIGS. 1-3 except with a modified mouthpiece, a main body panel which includes a bib, and an upper segment formed of a semi-transparent material which is worn contiguous with a wearer's eyes;

FIG. 8 is a plan view drawn on a scale of approximately 1:4 of the shield according to FIG. 7 viewed from the rear in which a downward extension of the modified upper segment is shown as a fragment;

FIG. 9 is an enlarged cross-sectional view taken substantially on the line IX—IX of FIG. 8.

Like reference characters indicate corresponding parts throughout the several views of the drawings.

DESCRIPTION OF THE PREFERRED EMBODIMENT

Figure 1:
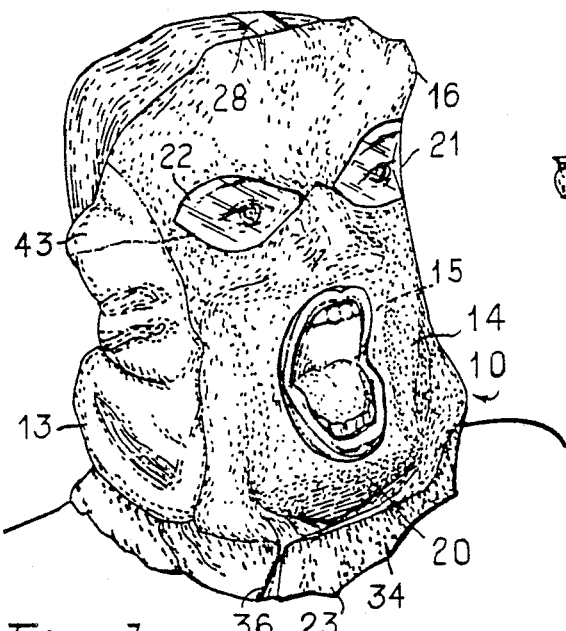
FIG. 1 is a perspective view of the front side of the head of a person wearing one embodiment of a face and neck shield according to the present invention.

Referring to FIG. 1 of the drawings, a disposable shield, designated generally at 10, is shown secured about a person's head so that the shield covers the frontal region of the individual's neck and all of his face with the exception of the mouth area. Those portions of the shield 10 contiguous with the lips are sealed thereabout as will be presently described so that the lips protrude through an opening 19 in it.

The shield 10 comprises a main body panel 11 formed integrally with respective side wings 12, 13 arranged symmetrically relative to the vertical centerline of the shield and affixed, with an adhesive, by heat sealing, or by stitching, to a central panel 14 having a mouthpiece 15. The central panel 14 is disposed in the breathing path, forwardly of a wearer's nostrils, and extends along this centerline in opposing directions from the mouthpiece 15 to points proximate the bridge of a wearer's nose and beneath his chin when the shield 10 is in use. The span of the panel 14 in a direction parallel with, as well as perpendicular to, the vertical centerline is at least three times the greatest transverse width of the opening 19; these longitudinal and transverse spans of the panel 14 measure, by way of example, 6.5 inches and 9 inches, respectively. Thus most of the surfaces of a wearer's cheeks, chin, and nose which are in contact with the shield 10 are contiguous with the panel 14.

Extending upwardly from the mid-section of the panel 14 and outwardly is an upper segment 16 which in the preferred embodiment has an upper convex edge. The extremities of the segment 16 at the end of this convex edge are joined to pieces 42, 43 which are attached to the wings 12, 13 generally outwardly of their upper junctures with the panel 14. Inwardly of these junctures, the panel 14 and the segment 16 define a pair of eye openings 17, 18.

Each of the side wings 12, 13 extends laterally from its juncture with the central panel 14 a distance which measures, by way of example, 7 inches so that the side wings contact the extremities of a wearer's cheeks when the shield 10 is worn. Further, in the preferred embodiment, tabs 24, 25; 26, 27 extend laterally from the wings 13, 12 and, together with the wings themselves, comprise means for securing the shield 10 on the user's face, the side wings 12, 13 being of sufficient size that one of the tabs 26 overlaps the other tab 24 at the back of the user's head (FIG. 4). By removing a backing protecting an adhesive coating on each of the tabs, they can be affixed to a proximate tab or other object to secure the shield 10 on a wearer's head. Similarly, the tab 28 extends outwardly from the upper convex edge of the segment 16 which at the points of attachment of the tab 28 thereto is spaced from the mouthpiece 15 by a distance which measures, by way of example, at least 8 inches. The tab 28 can be employed to hold the segment 16 in position during use.

The mouthpiece 15 is preferably fabricated from an air impermeable material having at least three laminated plies, one of which is formed from paper, plastic film or the like, and has a pressure sensitive adhesive coating on each side thereof which is protected by a backing (not shown) such as wax paper or polyethylene. During the assembly of the shield 10, one of these backings is removed; and the side of the mouthpiece 15 with its adhesive coating exposed is then affixed to the peripheral edges of an opening 19 formed in the central panel 14. The remaining backing is removed immediately prior to fitting the mouthpiece 15 about the lips of a patient.

A generally oval-shaped opening 19 in the mouthpiece 15 is sized and oriented so that the mouthpiece can be placed in contact with the skin proximate a person's lips while he holds them wide-open. In the preferred embodiment, the mouthpiece 15 is formed of a pliable material that is nevertheless sufficiently stiff that it aids a patient in so holding his mouth when the mouthpiece is sealed about his lips. The greatest transverse width and the greatest longitudinal length of the opening 19 in the mouthpiece 15 measure, by way of example, 2 inches and 3 inches, respectively. The mouthpiece 15 may have concentric lines of perforations (not shown) to enable a dental practioner to adjust the size of the opening in it quickly to accomodate variations between the mouths of individuals. In general, however, there is less than one-fourth inch of difference between the radii of curvature of the inner edges of the mouthpieces 15 which fit most adults. Thus ample variation in the opening 19 can be obtained by providing three sizes: small, medium, and large. Once it is properly sized and positioned, the mouthpiece 15 is pressed against the individual's face to form a seal surrounding his lips, which in use tends to prevent air carrying sodium bicarbonate and debris generated in his mouth during teeth cleaning and polishing from circumventing the shield 10 before such air reaches the remainder of his face.

Both the panel 14 and the segment 16 are preferably fabricated from an absorbent material such as gauze, towelling or the like through which there is a relatively free flow of air allowing ample ventilation of the region of the shield 10 proximate a wearer's nostrils while simultaneously filtering particulates and globules of moisture from the air passing through this region. The fineness of the mesh of the material forming the panel 14 as well as its nature and the number of layers of such material determine the efficiency with which it removes a mist of droplets. A panel 14 formed of two layers of 12-mesh gauze, by way of example, has been found adequate to remove the mist generated during the spraying of sodium bicarbonate solution in standard dental hygiene procedures. The segment 16 which is deployed proximate an individual's forehead, on the other hand, may be made from a single layer of 12-mesh gauze since the segment is not along the path traversed by the bulk of the air breathed by a wearer. In addition, the pieces 42, 43 extending from the segment 16 are preferably formed of the same material as the latter.

Figure 3:
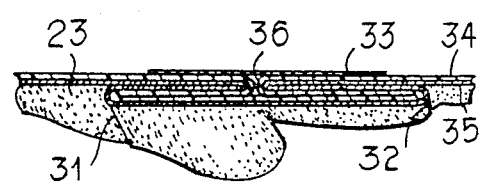
FIG. 3 is an enlarged cross-sectional view taken substantially on the line III—III of FIG. 2.
Figure 2:
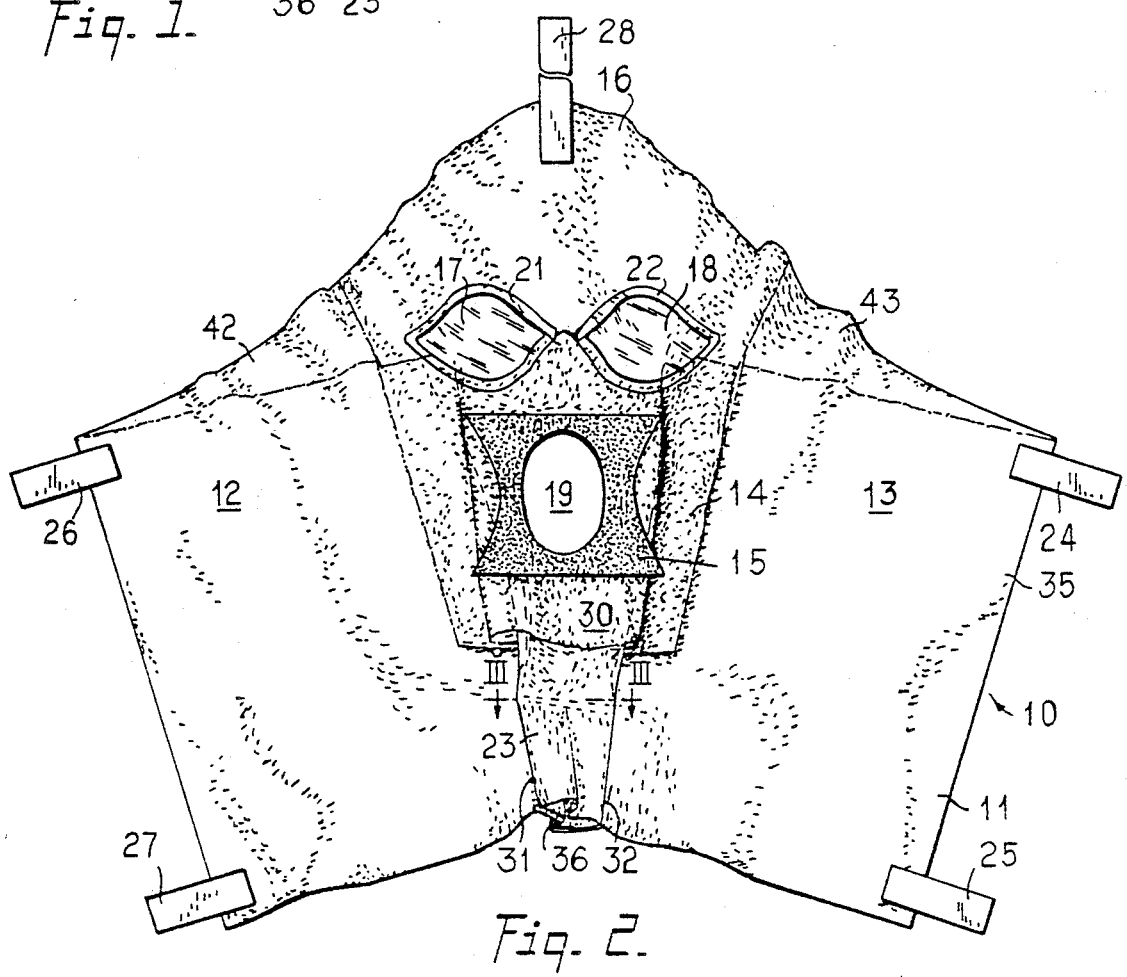
FIG. 2 is a plan view drawn on a scale of approximately 1:4 of the shield according to FIG. 1 viewed from the rear.
Figure 10:
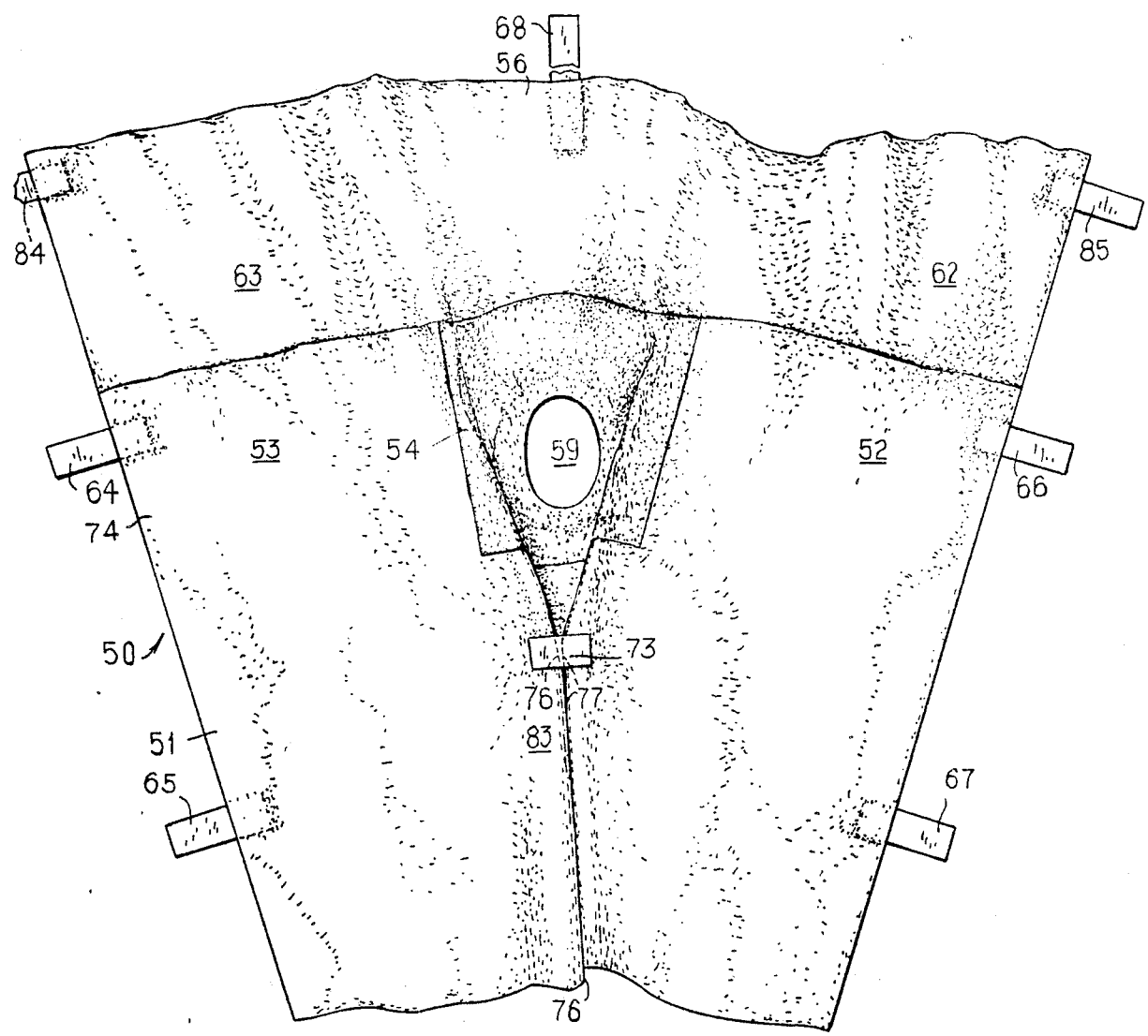
FIG. 10 is a plan view of the shield according to FIG. 7 viewed from the front.

At least as impervious to mists as the central panel 14 is the body panel 11 which, in the preferred embodiment, is fabricated from an absorbent paper 34 with a porosity substantially less than that of two layers of 12-mesh gauze. The paper 34 is backed by a liner 35 of polyethylene or the like, with both layers having a texture as a result of being joined together by a heat sealing treatment. As is best seen in FIGS. 2 and 3, the liner 35 is disposed on the inner side of the shield 10 as is the mouthpiece 15. The panel 11 tends to prevent any moisture condensing upon it, such as that generated by a high speed drill and during the spraying of bicarbonate solution, from running down a patient's neck. The panels 11, 14 and the segment 16 may be joined together with a tape having an adhesive coating on both sides thereof, by stitching, or the like; but in any case, the junctures between the panels 11, 14 and between them and the segment 16 are at least as impervious to mists as are the panels 11, 14 themselves.

Sections 21, 22 of thin, flexible, transparent material such as polyethylene, vinyl, or the like are affixed to the entire length of the edges of the eye openings 17, 18 and completely cover them, thereby protecting the eyes of a wearer while allowing him to view his surroundings. Moreover, by spanning each of the openings 17, 18 with a section 21, 22, these openings substantially retain their shape when the shield 10 is being worn regardless of the lack of stiffness of the materials employed to form the panel 14 and the segment 16.

Extending downwardly from the central panel 14 along its lower edge is a bridging section 23 sandwiched between the lower ends of the wings 12, 13. The section 23, which like the wings 12, 13 is an integral portion of the main body panel 11, measures, by way of example, 7 inches in a direction transverse to the centerline of the shield and about 6 inches in a direction parallel to this centerline. The section 23 is folded upon itself twice to form two pairs of pleats 31, 36; 32, 37, one pair being disposed on each side of the vertical centerline of the shield 10. Parts of the outer edges 36, 37 of the pleats disposed at a distance that measures, by way of example, approximately 4 inches from the lowermost edge of the opening 19 are then fixed together permanently by an application of an adhesive tape 33, by stitching, or by the like (FIGS. 2, 5 and 6). The pleats form a chamber 20 into which a wearer's chin protrudes as it comes into contact with a region 30 of the central panel below the mouthpiece 15. This contact and the formation of the chamber 20 conforming generally to the chin configuration of a human occur simultaneously with a tucking of the bulk of the bridging section 23 beneath a person's chin as illustrated in FIG. 1. The chamber 20 helps to insure that the mist of sodium bicarbonate solution as well as the debris-and-bacteria-laden air arising during a dental hygiene procedure passes through the filter supplied by the central panel 14 before reaching a patient's nostrils. Moreover, with the flexibility provided with these two pairs of pleats, a patient can turn his head from side to side with less twisting of the entire shield than would otherwise be possible and with little, if any, forces acting to break the seal between the mouthpiece 15 and his skin.

An alternate embodiment of the shield 10 includes a cap (not shown) of snap which is mounted on the inner side of the shield between the eye openings 17, 18 and which is engageable with a base of a snap attached to the bridge of a pair of safety glasses (not shown), thereby providing improved visibility for a wearer. Preferably, the glasses are reused while the shield is discarded after each use.

MODIFICATION

In FIGS. 1-6, a preferred embodiment of the present invention was shown and described in which portions of the upper edge of the central panel 14 and of the lower edge of the upper segment 16 define a pair of eye openings 17, 18. Alternately, there is provided a shield 50 having an upper segment 56 without any eye openings formed therein but which is formed of a semi-transparent material through which a wearer may obtain a partially obscured view of his surroundings. Fabrication of the upper segment 56 from a soft, featherweight, fibrous material such as Pellon TM or the like which has a finer average pore size than that of 12-mesh gauze is preferred.

In the alternate embodiment shown in FIGS. 7-10, the upper segment 56 has a downward extension 80 which overlays substantially an entire central panel 54 including a region 70 so that a wearer's chin comes into contact with the extension 80. The downward extension 80 measures, by way of example, 8 inches square. A mouthpiece 55 affixed to the peripheral edges of the extension 80 surrounds an opening 59 formed therein which is aligned with a opening of the same dimensions in the central panel 54. The extension 80 and the panel 54 are preferably joined to each other and the extension to the mouthpiece 55 along the peripheral edges of the opening 59 in such a manner that once the mouthpiece 55 is pressed against the user's face to form a seal surrounding his lips, air carrying sodium bicarbonate and debris generated in his mouth during teeth cleaning and polishing is prevented from circumventing the shield 50 before such air reaches the remainder of his face.

Moreover, the overlapping extension 80 so joined to the panel 54 allows the creation of a chamber 60 which is similar in configuration to the chamber 20 of the embodiment shown in FIGS. 1-6. A bridging section 83 extending downwardly from the panel 54 is folded upon itself twice to form a pair of pleats 71, 77; 72, 76 on each side of the vertical centerline of the shield 50; and parts of the outer edges of the pleats 76, 77 are then fixed together permanently by an application of an adhesive tape 73, by stitching or by the like (FIG. 9). These fixed parts of the pleats are disposed at a distance from the through opening 59 which measures, by way of example, at least 4 inches. The pleats 71, 77; 72, 76 form the chamber 60 into which a wearer's chin protrudes as it comes in contact with the lower portion of the extension 80.

A main body panel 51, the central panel 54, the mouthpiece 55 and tabs 64, 65, 66, 67, 68 are fabricated in each instance of the same materials as are the panels 11, 14; the mouthpiece 15; and the tabs 24, 25, 26, 27, 28, respectively, even though differences exist in the overall shape of these various elements as may be seen by comparing the two embodiments shown in FIGS. 1-10. In particular, the upper segment 56 in the alternate embodiment includes enlarged side pieces 62, 63 formed integrally with the segment 56 and having additional tabs 84, 85 to provide extra protection for a wearer's hair; and the bridging section 83 as well as the side wings 52, 53 formed integrally with the body panel 51 extend downwardly from the panel 54 a sufficient distance to protect the patient's upper body from spray-generated mist, thereby eliminating the need for an additional, separated bib to protect him.

As with the panel 11 in the embodiment shown in FIGS. 1-6, the main body panel 51 is fabricated from an absorbent paper 74 backed by a liner 75 of polyethylene or the like, with both layers having a texture as a result of being joined together by a heat sealing treatment. Moreover, the panel 51 is at least as impervious to mists as in the central panel 54. The panels 51, 54, and the segment 56 may be joined together with a tape having an adhesive coating on both sides thereof, by stitching, or by the like; but in any case, the junctures between the panels 51, 54 and between them and the segment 56 are at least as impervious to mists as are the panels 51, 54 themselves.

What is claimed is:

1. A facial shield for use on a patient's face in dental procedures comprising:
   (a) a central panel of air permeable, mist imperable material; a mouthpiece of air imperable, pliable material, the mouthpiece and the central panel having first and second openings, respectively; the central panel overlapping the entire outer peripheral edge of the mouthpiece, the first and second openings being disposed with respect to each other so as to form a through opening whcih is sized enough for the patient's open mouth;
   (b) the shield having an imaginary centerline which bisects the shield approximately symmetrically, the longitudinal axis of the through opening being disposed generally along the centerline; the central panel spanning in a direction parallel with, as well as perpendicular to, said centerline a distance which is at least three times the greatest transverse width of the through opening, the central panel being adapted to overlie the tip of the patient's nostrils;
   (c) the mouthpiece including first and second pressure-sensitive adhesive coatings on sides of the mouthpiece which face toward and away from the central panel, respectively; each pressure-sensitive adhesive coating surrounding said first opening, the first pressure-sensitive adhesive coating being disposed at least substantially at the outer peripheral edge of the mouthpiece, the second pressure-sensitive adhesive coating being disposed at least substantially at the inner peripheral edge of the mouthpiece; the central panel being affixed to the mouthpiece by the first pressure-sensitive adhesive coating; the second pressure-sensitive adhesive coating being adapted to adhere to the skin proximate the lips of the patient to form a seal between the skin and the mouthpiece which is disposed proximate to and extends along the entire length of the outer edge of the patient's lips;
   (d) an upper segment of a first flexible material which extends generally upwardly from the central panel;
   (e) a main body panel of a second flexible material having side wings and a section which extend laterally and downwardly, respectively, from the central panel; the span of the upper segment in a direction generally parallel to the centerline being at least as great as the greatest transverse width of the through opening, the span of the downwardly extending section and of each of the side wings in a direction parallel and perpendicular, respectively, to the centerline being at least as great as the greatest transverse width of the through opening; the main body panel, the central panel and the upper segment together being adapted to cover substantially the entire face of the patient; the main body panel and junctures between the side wings and the downwardly extending section and the central panel being at least as impervious to mists as is the central panel;
   (f) means for securing the side wings of the main body panel and the upper segment on the patient's face, the securing means being disposed proximate to edges of the side wings and of the upper segment which are situated distal from the central panel, the securing means including tabs attached to the side wings and to the upper segment, each tab having an inwardly facing side, the inwardly facing side being adapted to engage against the patient's head; the securing means further including a third pressure-sensitive adhesive coating on said inwardly facing side; and
   (g) the downwardly extending section being folded upon itself twice on both sides of said centerline to form two pairs of deep pleats generally parallel to the centerline, the edges of each of the pleats within each of said pairs being spaced from each other generally at a distance which is at least as great as one-half the greatest transverse width of the through opening; one side of the pleats of each pair being disposed outwardly; parts of the outwardly disposed edges of the pleats being contiguous and permanently fixed together along a portion of the centerline disposed downwardly of the mouthpiece, said fixed parts of the pleats being situated at a distance from the through opening which is at least one-half again as great as the greatest transverse width of the through opening, so that the pleats form a chamber above said fixed parts of the pleats which is adapted to receive the patient's chin, the flexibility afforded by the pleats helping to insure that the seal between the mouthpiece and the patient's skin is maintained intact as his head is turned from side to side.

2. A facial shield for use on a patient's face in dental procedures comprising:
   (a) a central panel of air permeable, mist impermeable material; a mouthpiece of air impermeable, pliable material, the mouthpiece and the central panel having first and second openings, respectively; the central panel overlapping the entire outer peripheral edge of the mouthpiece and being affixed thereto, the first and second openings being disposed with respect to each other so as to form a through opening which is sized large enough for the patient's open mouth;
   (b) the shield having an imaginary centerline which bisects the shield approximately symmetrically, the longitudinal axis of the through opening being disposed generally along the centerline; the central panel spanning in a direction parallel with, as well as perpendicular to, said centerline a distance which is at least three times the greatest transverse width of the through opening, the central panel being adapted to overlie the tip of the patient's nostrils;
   (c) the mouthpiece including first and second pressure-sensitive adhesive coatings on sides of the mouthpiece which face toward and away from the central panel, respectively; the first pressure-sensitive adhesive coating surrounding said first opening and being disposed at least substantially at the outer peripheral edge of the mouthpiece, the second pressure-sensitive adhesive coating being disposed at least substantially at the inner peripheral edge of the mouthpiece; the central panel being affixed to the mouthpiece by the first pressure-sensitive adhesive coating; the second pressure-sensitive adhesive coating being adapted to adhere to the skin proximate the lips of the patient to form a seal between the skin and the mouthpiece which is disposed proximate to and extends along the entire length of the outer edges of the patient's lips;
   (d) an upper segment of a first flexible material which extends generally upwardly from the centrl panel;

(e) a main body panel of a second flexible material having side wings and a section which extend laterally and downwardly, respectively, from the central panel; the span of the upper segment in a direction generally parallel to the centerline being at least as great as the greatest transverse width of the through opening, the span of the downwardly extending section and of each of the side wings in a direction parallel and perpendicular, respectively, to the centerline being at least as great as the greatest transverse width of the through opening; the main body panel, the central panel and the upper segment together being adapted to cover substantially the entire face of the patient; the main body panel and junctures between the side wings and the downwardly extending section and the central panel being at least as impervious to mists as is the central panel;

(f) means for securing the side wings of the main body panel and the upper segment on the patient's face; and (g) the downwardly extending section being folded upon itself twice on both sides of said centerline to form two pairs of pleats generally parallel to the centerline, one side of the pleats of each pair being disposed outwardly, the outwardly disposed side being adapted to face away from the patient's head; parts of the edges of the outwardly disposed sides of the pleats being contiguous and permanently fixed together along a portion of the centerline disposed downwardly of the mouthpiece, said fixed parts of the pleats being situated at a distance from the through opening which is at least one-half again as great as the greatest transverse width of the through opening, each of the pleats within each of said pairs being unfoldable above said fixed parts, so that the pleats can be spread apart to form a chamber above said fixed parts of the pleats which is adapted to receive the patient's chin, the flexibility afforded by the pleats helping to insure that the seal between the mouthpiece and the patient's skin is maintained intact as his head is turned from side to side.

3. A shield according to claim 2 wherein the securing means further comprises at least one tab affixed to an edge of each of the side wings and to the upper segment distal from the central panel, each tab having an inwardly facing side which is adapted to engage against the patient's head, the tab having a third pressure-sensitive adhesive coating on the inwardly facing side.

4. A facial shield for use on a patient's face in dental procedures comprising:

(a) a central panel of air permeable, mist impermeable material having a first opening;

(b) an upper segment formed of a first flexible material, the upper segment having a downward extension which is joined to the central panel along the upper edge thereof and which overlaps the central panel, the downward extension being adapted to engage against the patient's face;

(c) a mouthpiece of air impermeable, pliable material, the mouthpiece and the downward extension having second and third openings, respectively; the downward extension overlapping the entire outer peripheral edge of the mouthpiece and being affixed thereto, portions of the downward extension along the peripheral edge of the third opening being joined to the central panel proximate the first opening; the first, second, and third openings being disposed with respect to each other so as to form a through opening which is sized large enough for the patient's open mouth;

(d) the shield having an imaginary centerline which bisects the shield approximately symmetrically, the longitudinal axis of the through opening being disposed generally along the centerline; the central panel spanning in a direction parallel with, as well as perpendicular to, said centerline a distance which is at least three times the greatest transverse width of the through opening, the central panel being adapted to cover the top of the patient's nostrils;

(e) the mouthpiece including a first pressure-sensitive adhesive coating on a side of the mouthpiece which faces away from the downward extension, the first pressure-sensitive adhesive coating surrounding said second opening and being disposed at least substantially at the inner edge of the mouthpiece; the mouthpice being adapted to adhere to the skin proximate the lips of the patient to form a seal between the mouthpiece and the skin surrounding the lips;

(f) main body panel of a second flexible material having side wings and a section which extend laterally and downwardly, respectively, from the central panel; the span of a portion of the upper segment disposed upwardly of said upper edge in a direction generally parallel to the centerline being at least as great as the greatest transverse width of the through opening, the span of the downwardly extending section and of each of the side wings in a direction parallel and perpendicular, respectively, to said centerline being at least as great as the greatest transverse width of the through opening; the main body panel, the central panel and the upper segment together being adapted to cover substantially the entire face of the patient;

(g) means for securing the side wings of the main body panel and the upper segment on the patient's face; and (h) the downwardly extending section being folded upon itself twice on both sides of said centerline to form two pairs of pleats generally parallel to the centerline, one side of the pleats of each pair being disposed outwardly, the outwardly disposed sides being adapted to face away from the patient's head; parts of the edges of the outwardly disposed sides of the plates being contiguous and permanently fixed together along a portion of said centerline disposed downwardly of the mouthpiece, said fixed parts of the edges of the outwardly disposed sides of the pleats being situated at a distance from the through opening which is generally one-half again as large as the greatest transverse width of the through opening, each of the pleats within each of said pairs being unfoldable above said fixed parts, so that the pleats can be spread apart to form a chamber above said fixed parts which is adapted to receive the patient's chin, the flexibility afforded by the pleats helping to insure that the seal between the mouthpiece and the patient's skin is maintained intact as his head is turned from side to side.

* * * * *